Figure 1:
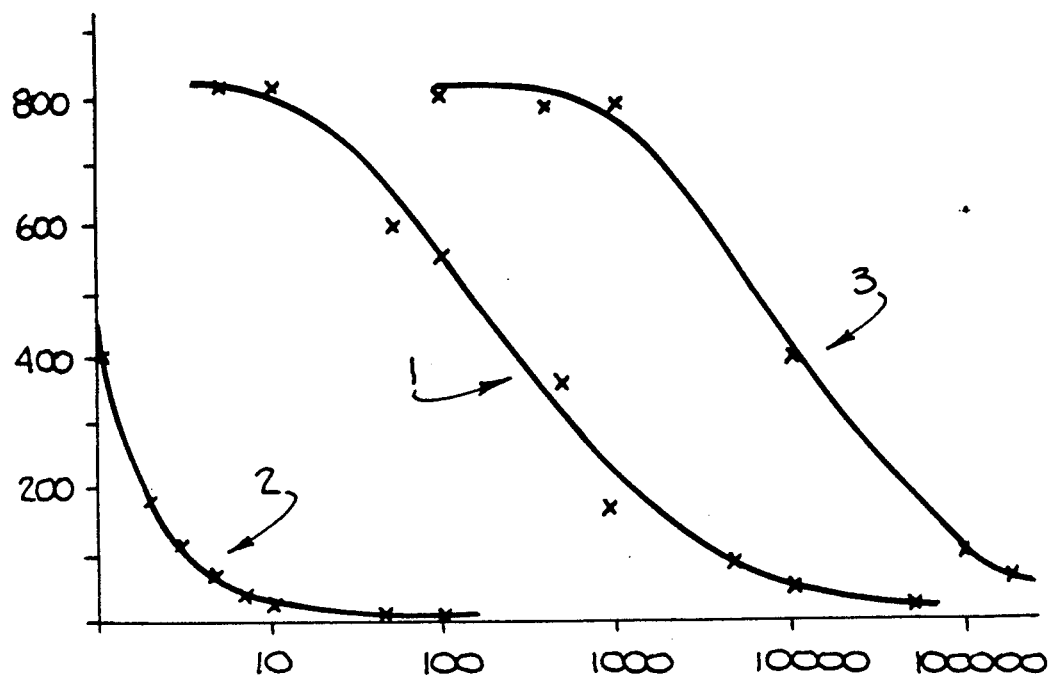

United States Patent [19]  
Wilk et al.

[11] Patent Number: 5,037,764
[45] Date of Patent: Aug. 6, 1991

[54] PROCESS FOR DETERMINATION OF AN ANALYTE AND REAGENT THEREFOR

[75] Inventors: Hans-Erich Wilk, Lorsch; Helmut Freitag, Weinheim; Josef Burg, Krailling, all of Fed. Rep. of Germany; Johann Berger, Indianapolis, Ind.

[73] Assignee: Boehringer Mannheim GmbH, Mannheim, Fed. Rep. of Germany

[21] Appl. No.: 73,989

[22] Filed: Jul. 16, 1987

[30] Foreign Application Priority Data

Jul. 19, 1986 [DE] Fed. Rep. of Germany ....... 3624464

[51] Int. Cl.$^5$ .......................................... G01N 33/543
[52] U.S. Cl. .................................... 436/518; 436/524; 436/527; 436/533; 436/534; 436/528; 435/7.92
[58] Field of Search ............... 436/518, 524, 527–531, 436/512, 533, 534; 435/7

[56] References Cited

U.S. PATENT DOCUMENTS 4,243,749 1/1981 Sadeh et al. ............... 436/531
4,366,143 12/1982 Midgley et al. .
4,378,428 3/1983 Farina et al. ............... 431/528

FOREIGN PATENT DOCUMENTS 0026103 4/1981 European Pat. Off. .
0089806 9/1983 European Pat. Off. .
0106615 4/1984 European Pat. Off. .
0182385 11/1984 European Pat. Off. .
8303306 9/1983 PCT Int'l Appl. .
8500226 1/1985 PCT Int'l Appl. .

Primary Examiner—Robert J. Warden
Assistant Examiner—Lyle A. Alexander
Attorney, Agent, or Firm—Felfe & Lynch

[57] ABSTRACT

The present invention provides a process for the detection of an analyte, wherein a sample containing the analyte is incubated either with a labelled binding partner and the immobilized analyte or an immobilized analyte analogue or with the labelled analyte or analyte analogue and an immobilized binding partner, the binding partner displaying towards the immobilized or labelled analyte or analyte analogue a higher affinity than towards the free analyte, and the labelled binding partner or the labelled analyte or the labelled analyte analogue is present in insufficiency compared with the concentration of the analyte to be detected.

The present invention also provides an agent for carrying out this process, wherein it contains either the immobilized analyte or an immobilized analyte analogue and a labelled binding partner or the labelled analyte or a labelled analyte analogue and an immobilized binding partner, as well as optionally an appropriate buffer system and further conventionally used adjuvants, the binding partner displaying towards the immobilized or labelled analyte or analyte analogue a higher affinity than towards the free analyte.

22 Claims, 2 Drawing Sheets

PROCESS FOR DETERMINATION OF AN ANALYTE AND REAGENT THEREFOR

The present invention is concerned with a process for the detection of an analyte in a sample, as well as with an agent suitable for this process.

For many years, immunological detection processes have played an important part in clinical diagnosis. They are characterised in that they are highly specific and extremely sensitive. These detection processes are based upon the immunological exchange action between the analyte to be detected and its binding partner or partners. By labelling one of the binding partners, the degree of reaction and thus the concentration of the analyte to be measured can be determined. The immunological determination processes differ, depending upon the selected labelling, for example radio-immunoassay (radioactive labelling), enzyme immunoassay (enzyme labelling), fluorescence immunoassay (fluorescence label) and the like.

A disadvantage of these methods is that, in some cases, very long incubation times are necessary and the detection processes are very labour-intensive. In the case of the radio-immunoassays, there are also the difficulties which are involved with the handling of radioactive substances.

Therefore, attempts have not been lacking to improve these tests. Thus, for example, a measurement process, which is especially preferred for many purposes, takes place in such a manner that the analyte to be measured is first incubated with an excess of the labelled binding partner. The labelled binding partner not bound by the analyte is fixed with the help of carrier-bound analytes. After a usual separation of the bound from the non-bound part, the original analyte content of the sample can be determined on the basis of the labelling.

Like all other immunological processes, this measurement principle displays a very high sensitivity but, in addition, has the advantage that it can be carried out more quickly than the previously usual test procedures. However, an important disadvantage of this variant is that the labelled binding partner of the analyte to be determined must be used in excess, i.e. relatively large amounts of labelled immunological binding partners are needed. The detection of highly concentrated analytes in undiluted blood, serum or plasma is, because of the necessarily high concentration of antibody and the costs involved therewith, scarcely capable of being carried out.

Therefore, it is an object of the present invention to provide a process in which not so high concentrations of labelled binding partners are necessary and which, therefore, can be carried out more cost-favourably than the previously known processes.

Thus, according to the present invention, there is provided a process for the detection of an analyte, wherein a sample containing the analyte is incubated either with a labelled binding partner and the immobilised analyte or an immobilised analyte analogue or with the labelled analyte or analyte analogue and an immobilised binding partner, the binding partner displaying towards the immobilised or labelled analyte or analyte analogue a higher affinity than towards the free analyte, and the labelled binding partner or the labelled analyte or the labelled analyte analogue is present in insufficiency compared with the concentration of the analyte to be detected.

By an analyte, there is understood, quite generally, a substance which can enter into a specific exchange action with a suitable binding partner. Hereunder is to be understood, for example, every kind of exchange action, for example an antigen-antibody, enzyme-coenzyme or also any other ligand-receptor exchange action. The analyte is preferably a hapten, for example theophylline, thyroxin (T4), phenobarbital or the like, an antigen, for example a nucleic acid or a protein, such as human choriogonadotropin (hCG), human serum albumin (HSA), carcinoembrionic antigen (CEA), α-foetoprotein (AFP), glycosylated hemoglobin (HbA$_1$), immunoglobulins or the like, or also an antibody. The binding partner is determined by the particular analyte. If the analyte is, for example, a hapten or antigen, then, as binding partner, there is needed an antibody directed against this hapten or antigen; if an antibody is to be determined, then, as binding partner, a related antigen or hapten or anti-antibody is necessary.

By an analyte analogue there is to be understood, according to the present invention, a compound which displays a structural relationship with the analyte and thus also related binding properties. Such analyte/analyte analogue pairs include, for example, T3/T4 theophylline/theobromine, human serum albumin/monkey serum albumin. As an analyte analogue, there can also be used anti-idiotypical antibodies which are directed against the antigen binding points. Such antibodies automatically have a structural relationship with the analyte to be determined.

By antibodies in the meaning of the present invention are to be understood not only monoclonal but also polyclonal antibodies. They can be used as complete antibodies or also in the form of antibody fragments, for example Fab fragments. According to the present invention, there are used antibodies which recognize and more firmly bind the carrier-bound or labelled analytes or the carrier-bound or labelled analyte analogue more specifically than the free analytes.

Such antibodies include, for example, antibodies which co-recognize the bridge member with which the analyte or the analyte analogue is bound to the carrier matrix or to the labelling material. Such antibodies can be obtained according to known methods, whereby, for the immunization, a substance is used which consists of the analyte or the analyte analogue and the bridge member, as well as, if the analyte or the analyte analogue is itself not immunogenically active, an immunogenic protein, for example albumin, edestin or the like.

Antibodies can also be used which recognize the analyte analogue specifically and cross-react with the actual analyte only with low affinity. Thus, for example, according to the process of the present invention, T4 can be determined when T3 is bound to the carrier matrix and an antibody is used which has a high affinity towards T3 but only little affinity towards T4. Proteins can also be determined in an analogous way. Thus, in the manner according to the present invention, human serum albumin (HSA) can be detected in that monkey serum albumin is bound to the solid phase and the antibody is directed against the monkey serum albumin with less cross-reactivity to human serum albumin. The analyte can also be determined when, as analyte analogue, a particular part structure or part sequence is bound to the carrier matrix and an antibody is used which recognizes this immobilized part structure or part sequence more specifically than the analyte to be detected. This variant can be advantageously utilized, for example, for the detection of glycosylated hemoglobin in that, on the solid phase, there is bound a synthetic peptide with the glycosylated place of the glycosylated hemoglobin and an antibody against this peptide is used.

With the help of such antibodies, it is possible, in the process according to the present invention, to use the enzyme-labelled binding partner or the labelled analyte or the labelled analyte analogue in an insufficiency with regard to the analyte to be determined. How different the concentrations of analyte to be determined and labelled binding partner or labelled analyte or analyte analogue can be depends decisively upon how great is the affinity difference of the binding partner towards the free analyte and the immobilized or labelled analyte or analyte analogue. The lower the affinity of the binding partner toward the free analyte in comparison with the bound or labelled analyte or analyte analogue, the lower the possible concentration of the labelled binding partner or of the labelled analyte or analyte analogue in comparison to the concentration of the analyte to be determined. It has been found that the process according to the present invention can be carried out advantageously at a concentration ratio of labelled binding partner or labelled analyte or analyte analogue to analyte to be determined of up to 1:10,000 when the binding partner used displays an affinity difference of the same order of magnitude. A concentration ratio of 1:2 to 1:3000 has been shown to be especially advantageous.

In the case of the incubation of the sample which contains the analyte to be determined with the labelled binding partner and the carrier bound analyte or analyte analogue, the following reactions compete essentially with one another:

In these equations, A is the analyte to be measured, B is the binding partner directed against the analyte, M is the labelling agent and $A_{fix}$ is the analyte or analyte analogue bound to the carrier.

According to equation (1), the immunological complex A-B-M is formed from the analyte and the labelled binding partner B-M. Because of the great excess of the analyte, this equilibrium is substantially displaced to the side of the labelled immunological complex so that, in the reaction mixture, there is present almost exclusively complex and excess free analyte. Because of the higher affinity of the binding partner towards the bound analyte $A_{fix}$, a displacement reaction according to equation (2) takes place. The higher the concentration of the analyte to be detected in the sample, the less the displacement of the analyte A to be detected from the immunological complex A-B-M by the carrier-bound analyte or analyte analogue $A_{fix}$. Consequently, the concentration of the analyte in the sample is proportional to the amount of the labelling in the soluble part of the reaction mixture or, vice versa, inversely proportional to the amount of the labelling which is bound to the carrier via $A_{fix}$. By measurement of the labelling bound to the carrier or also of the labelling present in the solution, there can be deduced the concentration of the analyte in the sample.

Analogous equations can be formulated and analogous considerations can be made for the case in which the sample is incubated with the labelled analyte or a labelled analyte analogue and an immobilized binding partner.

The process according to the present invention can be carried out advantageously in that the sample to be investigated containing the analyte to be detected is first pre-incubated with the labelled binding partner. This incubation mixture is subsequently brought into contact with the solid phase to which is bound the analyte or an analyte analogue. It is followed by a usual separation of the bound from the non-bound part. As the last step, the labelling is determined in the free and/or bound part and, from this, a conclusion can be made about the analyte content of the sample.

The process can also be carried out in such a manner that the sample to be investigated, the labelled binding partner and the analyte or analyte analogue bound to a carrier is simultaneously incubated. After the incubation step, the bound and non-bound part is again separated, the labelling is determined in the bound and/or in the non-bound part and, from this, a conclusion is made about the concentration of the analyte in the sample.

Such a one-step test process can be carried out, for example, in the form of a usual microtitre test. For this purpose, the analyte is first immobilised on the microtitre plate. Thereafter, it is incubated with a mixture of labelled binding partner and the sample with the analyte to be determined. After a definite incubation time, the solution is removed, washing is carried out and subsequently the amount of labelling agent bound to the microtitre plate is measured.

The above-described process variant can also be readily carried out when, instead of the labelled binding partner, there is used the labelled analyte or a labelled analyte analogue and, instead of the immobilised analyte or analyte analogue, there is used an immobilised binding partner.

The binding partner or the analyte or the analyte analogue can be labelled in the usual way. A whole series of known labelling agents are available, for example labelling with a radio-active isotope, with an enzyme, with a fluorescing substance or with some other substance which can be detected photometrically. In the scope of the present invention, labelling with enzymes is especially preferred. As labelling enzyme, there can be used, for example, peroxidase, alkaline phosphatase, glucose oxidase or, most preferably β-galactosidase.

The binding of the analyte or of the analyte analogue or also of the binding partner to a carrier also takes place in a conventional manner. For this purpose, one utilizes reactive groups of the analyte, of the analyte analogue or of the binding partner. If these substances do not possess suitable reactive groups, such groups can be introduced into the molecule according to known methods. Via these reactive groups one attaches the molecule to the reactive groups of the carrier material, usually with the insertion of a bifunctional bridge member. The binding partner can also be applied to the carrier adsorptively. As carrier materials, there can be used all materials normally employed for the immobilization of immunologically-active, biochemical compounds, including nitrocellulose, papers, synthetic resin particles of polystyrene and the like.

The present invention also provides an agent for carrying out the process according to the present invention. This agent contains either the immobilized analyte or an immobilized analyte analogue and a labelled binding partner or the labelled analyte or a labelled analyte analogue and an immobilized binding partner, as well as possibly an appropriate buffer system and, may also contain adjuvant materials, such as those used in standard assays. In these agents, which may be in the form of kits containing separate portions of each component, the binding partner displays towards the immobilized or labelled analyte or analyte analogue a higher affinity than towards the free analyte.

Samples of adjuvant materials as described supra include, for example, wetting agents, stabilizing agents, galenical adjuvant agents, structure formers and the like.

If, for the detection of the labelling agent, further substances are necessary, then these can also be present in the reagent. If, as labelling agent, for example an enzyme is used, then the substrate and other adjuvant materials necessary for the detection of this enzyme are advantageously added to the agent.

The agent can be produced in the most varied ways. It can consist, for example, of different solutions which contain the labelled binding partner or the labelled analyte or the labelled analyte analogue, an appropriate buffer system and detection materials for the determination of the labelling agent, as well as possibly further adjuvant materials, and of a solid phase to which is bound the analyte or the analyte analogue or the binding partner, possibly via a bridge member. As solvent, there can be used water or a mixture of water with a water-soluble organic solvent, for example methanol, ethanol, acetone or dimethylformamide. For reasons of storage stability, it can be advantageous to divide the reagents needed for the test into two or more solutions which are first brought together when carrying out the actual investigation.

For certain embodiments of the agent according to the present invention, it may be preferred to have a component or components of the agent present in part or completely in lyophilized form. For this purpose, solutions of the component materials in question are first prepared in the usual way and these are then freeze-dried in known manner. Before use, the lyophilizates are reconstituted in the usual way with an appropriate solvent, for example water.

It may also be preferred to produce individual components or all of the components of the agent according to the present invention in the form of powder mixtures or reagent tablets. For this purpose, the components of the agent are mixed with conventional galenical additive materials and granulated. Such additive materials include, for example, carbohydrates, such as mono-, oligo- and polysaccharides, sugar alcohols, such as mannitol, sorbitol and xylitol, and other inert compounds, such as polyethylene glycols and polyvinylpyrrolidone.

Furthermore, it is possible to apply individual components or also all of the components of the agent to a carrier and especially to an absorbent carrier, or to incorporate them into a carrier. It is also useful to apply or to incorporate the reagent components to various carriers or absorbent carriers and to combine these different carriers with one another in appropriate manner. Thus, an especially preferred embodiment of the reagent according to the present invention is constructed in such a manner that the labelled binding partner is contained on a first carrier, the analyte or analyte analogue is applied in immobilized form to a further carrier material and possibly a third carrier contains the reagent components necessary for the detection of the labelling agent. These three layers are so bound with one another that the sample is first applied to the first carrier with the labelled binding partner. The reaction between the analyte to be determined and the labelled binding partner here takes place. The reaction mixture is then brought into contact with the second layer which contains the bound analyte or the bound analyte analogue, the displacement reaction thereby taking place. The portion of the labelled binding partner bound by the analyte or analyte analogue fixed on the carrier remains adhering to this carrier matrix. The so-called "free" portion of the labelled binding partner bound with the analyte to be determined is then transferred to the third layer on which the detection of the labelling agent can be determined, for example on the basis of a colour reaction or photometrically. The transport of the reaction mixture through the individual layers can take place mechanically, for example by applying pressure, or also by diffusion or capillary force.

The following Examples are given for the purpose of illustrating the present invention:

EXAMPLE 1

Detection of Theophylline

A) Production of a polyclonal antibody against theophylline-9-carboxypentyledestin Sheep are immunized in known manner with theophylline-9-carboxypentyledestin. An antibody solution is isolated in known manner from the antisera taken from the sheep and the antibody solution is purified over theophylline-9-pentyl-Sepharose, elution taking place with graduated theophylline gradients. The fraction which is obtained with a high theophylline concentration is, after dialysis, further used.

B) Analysis with the antibodies obtained

Theophylline-9-carboxypentylhydroxysuccinimide ester is coupled to rabbit IgG (non-specific). The so-obtained polyhaptens (PH) are mixed with bicarbonate buffer (200 mmolar, pH 9.4) (10 μg. polyhapten/ml. of carbonate buffer). A microtiter plate is coated with this polyhapten solution.

The antibodies described in A) are diluted with incubation buffer (PBS, 1% bovine serum albumin, 0.1% TWEEN 20) so that a $10^{-8}$ solution is obtained. One part by volume of this solution is mixed with the same volume of a serological dilution series (factor $1:2^n$) of theophylline, theophylline-9-carboxypentyl-N-t-BOC-lysine or caffeine and incubated for one hour at ambient temperature. (N-t-BOC is an abbreviation for the tert.-butyloxycarbonyl radical which is a conventionally used nitrogen protective group).

These incubation batches are applied to microtitre plates coated with polyhapten, followed by incubation for a further hour at ambient temperature. Thereafter, the solution is removed and washed several times. Finally, into the microtitre plate is applied rabbit anti-sheep antibody labelled with peroxidase (100 mU/ml.), followed by incubation for one hour at ambient temperature and subsequent washing. Into each hollow of the microtitre plate is introduced 100 μl. ABTS substrate solution (ABTS=2,2'-azino-d-(3-ethyl-benzthiazoline-6-sulphonic acid). After one hour, the extinction is determined with a micro-ELISA reader. Typical measurement curves are shown in FIG. 1 of the accompanying drawings. In this Figure:

(1) is the curve for theophylline (2) is the curve for theophylline-9-carboxypentyl-N-t-BOC-lysine (3) is the curve for caffeine It can be read off therefrom that an affinity difference of a factor 200 to 400 exists in the case of an acceptable cross-reaction of 2.5% with caffeine.

C) Detection of theophylline

The detection of theophylline takes place completely analogously to the process described above in B).

20 µl. theophylline-containing serum and 20 µl. of the above-mentioned antibody solution are incubated in the way described above under B) and analysed on a microtitre plate pre-coated according to B). First, with the help of serum samples which contain a precise, known amount, namely 2.5, 5, 10, 20 and 40 mg./liter theophylline, the following calibration table is obtained:

| $C_{theo}$ | mE |
| --- | --- |
| 2.5 | 490 |
| 5 | 392 |
| 10 | 300 |
| 20 | 224 |
| 40 | 143 |

The unknown theophylline content in samples is determined on the basis of this Table.

EXAMPLE 2

Detection of Thyroxin (T4)

A) Production of a monoclonal antibody against tetraiodothyronine-N-t-BOC-edestin Female balb/c mice are immunized in known manner with T4-N-t-BOC-edestin. Spleen cells of these immunised mice are fusioned with the myeloma cell line Ag 8.653 according to the known method of Köhler and Milstein. Clones obtained are selectioned. These clones are selected which possess a high affinity for T4-N-t-BOC-immunoglobulin.

Figure 2:
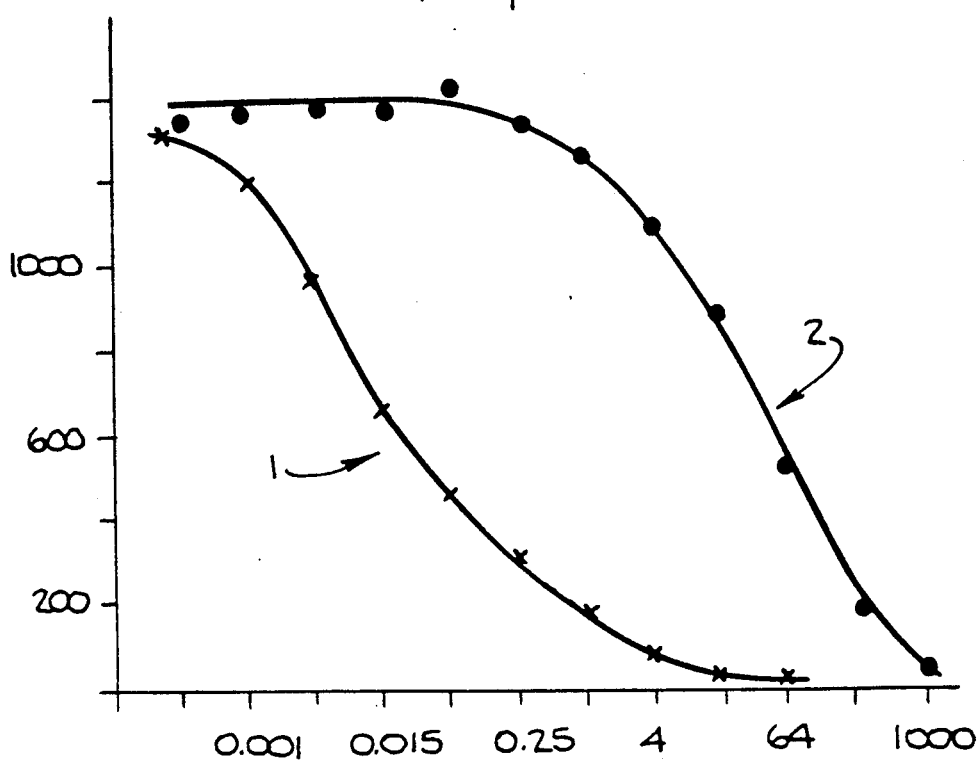

For the selection, the antibodies are incubated with a concentration series of T4 (factor $1:4^n$) (one hour at ambient temperature) and thereafter transferred to a PH-coated microtitre plate. After a further two hours incubation, the supernatant solution is removed, the plates washed and, analogously to Example 1, the bound antibody made visible with peroxidase-labelled anti-mouse antibodies and ABTS. FIG. 2 of the accompanying drawings shows the competition curve of such an antibody against modified T4 (curve 2) in comparison with a curve which has been obtained with an anti-T4 antibody which is directed against T4 (curve 1). An affinity difference of a factor of 2000 can be seen.

B) Conjugation of the monoclonal antibody with β-galactosidase

Purified monoclonal antibodies or Fab fragments obtained herefrom are reacted with maleimidohexanoylhydroxysuccinimide (MHS). The MHS-modified antibodies or antibody fragments are reacted with β-galactosidase. The reaction mixture is separated via gel filtration (Sephacryl S 400). A conjugate was used which is in the molecular weight range of 700,000 to 20,000,000 D.

C) Detection of tetraiodothyronine

Microtitre plates are coated analogously to section A) above with tetraiodothyronine-t-BOC-immunoglobulin (1 µg./ml.). Serum samples (50 µl.) with 0, 6, 25, 50, 125 and 247 µg./liter of tetraiodothyronine (for the preparation of these serum samples, there is used TBG-free standard serum, Boehringer Mannheim) are filled into the hollows of the microtitre plates and mixed with 150 µl. antibody-β-galactosidase conjugate (20 mU/ml.). After incubation for one hour at ambient temperature, the supernatant is removed and the microtitre plate is washed and each hollow filled with 200 µl. substrate (1 mmole chlorophenol red galactoside, prepared according to Federal Republic of Germany Patent Specification No. 33 45 748). The calibration table obtained herefrom is given in the following:

| $C_{T4}$ (µg./l.) | mE |
| --- | --- |
| 0 | 620 |
| 6 | 596 |
| 25 | 519 |
| 50 | 433 |
| 125 | 320 |
| 247 | 225 |

Serum samples with an unknown T4 content can be determined on the basis of this calibration table.

EXAMPLE 3

Test Strips with Low-Affinity Antibodies for the Determination of Theophylline Monoclonal antibodies are produced in known manner with the help of the immunogen theophylline-8-carboxypropyledestin.

The antibodies are selected by competition experiments: 10 µl. amounts of antibody solution and 10 µl. of a theophylline concentration series ($5 \times 10^{-4}$M to $6 \times 10^{-8}$M theophylline in PBS) are incubated for two hours in a theophylline-8-carboxypropyl-rabbit IgG-coated microtitre plate. The batch is then removed from the microtitre plate, the plate is washed and the antibody bound to the polyhapten made visible as in Example 1 B).

Antibodies are selected, the binding of which to the polyhapten-coated plates could only be competed with large amounts of theophylline ($>2 \times 10^{-5}$M).

The complete antibodies or the antibody fragments are linked with β-galactosidase as described in Example 2 under B).

Production of the Solid Carrier Layers

A) Conjugate carrier

Filter paper (liquid take-up about 10 µl./cm²) is impregnated with a solution which contains 100 U/ml. anti-theophylline-8-carboxypropyledestin antibody 1% bovine serum albumin 1 mmole magnesium chloride and 25 mmole hepes/sodium hydroxide, pH 7.2.

The filter paper is subsequently dried.

B) Polyhapten matrix

The hapten is applied to a nitrocellulose membrane (0.2 µpore size). For this purpose, the membrane is incubated for 12 to 16 hours with polyhapten solution (3 mg./ml. polyhapten in PBS). Thereafter, it is afterloaded for two hours with 1 mg./ml. bovine serum albumin and washed for 30 minutes with 0.05% Triton X-100 in PBS.

C) Substrate carrier

Filter paper (liquid take-up about 10 µl./cm²) is impregnated in the usual way with a solution which contains 0.4% Tween 20

3 mM chlorophenol red galactoside
25 mM hepes/sodium hydroxide, pH 7.2

D) Test-strips

Figure 4:
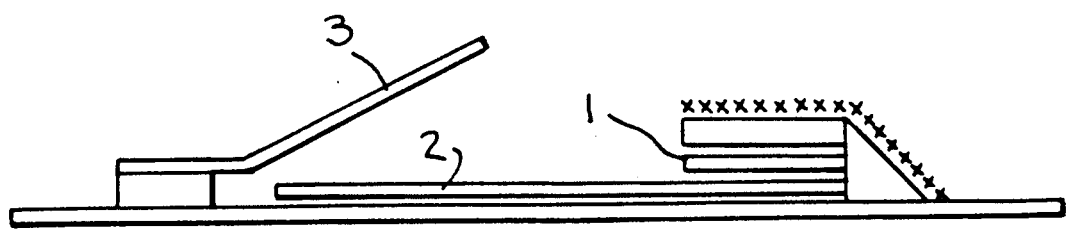

With these layers is produced the test strip shown in FIG. 4 of the accompanying drawings, the plasma separation being according to Federal Republic of Germany Patent Specification No. 30 29 579, and U.S. Pat. No. 4,477,575, the disclosure of which is incorporated by reference herein.

E) Measurement

Figure 3:
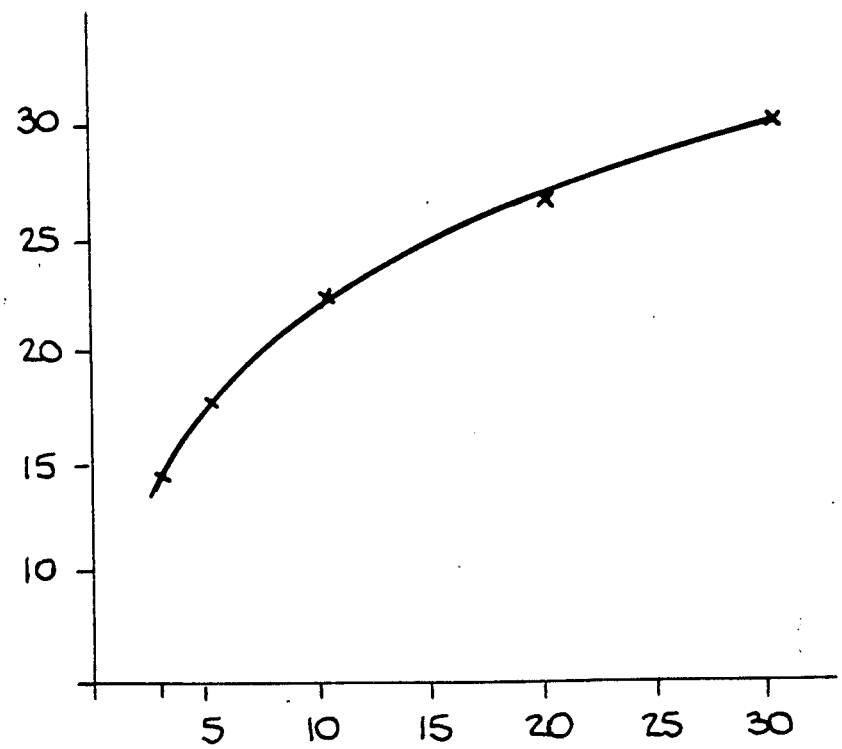

The sample (30 μl. whole blood, serum or the like) is applied to the glass fibre fleece and diffuses to the conjugate on carrier 1. This is thereby dissolved and interacts with the analyte present in the sample. The solution mixture passes to the polyhapten membrane 2 and is chromatographed thereover. Thereafter, the flap with the substrate carrier 3 is pressed on to the matrix 2. The part of the solution mixture not retained by the hapten matrix at the start of the matrix comes into contact with the substrate, the enzyme-substrate reaction taking place. After 20 seconds, the color development is determined by reflection photometry on the end of the polyhapten matrix (Δ% R = change of the reflection in % of the light shone in after 20 seconds). On the basis of samples with known theophylline concentrations, there is obtained the calibration curve shown in FIG. 3 of the accompanying drawings which covers the whole therapeutically relevant range. With the help of this calibration curve, the theophylline concentration in unknown samples is determined.

EXAMPLE 4

Determination of Phenytoin by means of Low-Affinity Antibodies

A) Production of the low-affinity antibodies

The antibodies are produced analogously to Example 1 A) by immunization of sheep with diphenylhydantoin-valeric acid-bovine serum albumin. Tests for the competitiveness are carried out analogously to Example 3 A). They show that a relatively high concentration ($6 \times 10^{-6}$M) of phenytoin is necessary for the competition of the polyhapten (antibody concentration: about $5 \times 10^{-8}$M, determined by absorption at 280 nm). Therefore, the antisera are not further fractionated.

V) Production of the test element

The determination process is carried out according to the method described in European Patent Specification No. 0,073,513. There is used the insert element for a centrifugal automatic analyser described therein in FIGS. 1 a and 1 b. This insert element contains seven chambers connected with one another which, in part, contain different fleece and are dosed successively under the influence of centrifugal force. The fleece are impregnated with different impregnation solutions.

The following fleece and impregnation solutions for the fleece are employed:

| | |
|---|---|
| Fleece 1: impregnation solution: | filter paper 3% wetting agent (Tween 20) |
| Fleece 2: impregnation solution | filter paper 100 mmole sodium phosphate buffer, pH 7.2 5 mmole EDTA 1% bovine serum albumin 0.75% wetting agent (Tween 20) |
| Fleece 3: impregnation solution: | filter paper anti-phenytoin antibody from sheep, prepared according to A), labelled with β-galactosidase, 100 mU/ml. activity, determined with o-nitrophenylgalactoside as substrate, 1% bovine serum albumin, 4 mmole magnesium aspartate, 50 mmole hepes buffer, pH 7.2 |
| Fleece 4: impregnation solution: | filter paper 2 μg./ml. rabbit immunoglobulin G which has been derivatized with diphenylhydantoin valeric acid, 4 μg./ml. sheep anti-rabbit Fc antibody produced according to Federal Republic of Germany Patent Specification No. 34 46 636 |
| Fleece 5: impregnation solution: | filter paper 15 mole chlorophenol red galactoside prepared according to U.S. Pat. No. 4.668.622 |

The chambers of the insert element are loaded as follows:

chamber 1: 1 fleece 1
chamber 2: empty
chamber 3: 1 fleece 2
chamber 4: 1 fleece 3
chamber 5: 1 fleece 4
chamber 6: 2 fleece 5
chamber 7: measurement cuvette.

C) Carrying out of the measurement

The serum used as sample solution is diluted 1:100 with 0.9% aqueous sodium chloride solution. 60 μl. of the so obtained solution are pipetted into the sample application chamber of the insert element and then the following centrifuging program carried out:

25 seconds 250 rpm
dissolving off of the detergent, buffer and conjugate; start of the first incubation
20 seconds 2000 rpm
300 seconds 600 rpm
incubation of sample and anti-phenytoin-antibody conjugate
300 seconds 0 rpm
incubation with carrier-fixed spaced phenytoin
15 seconds 2000 rpm
ending of the second incubation
15 seconds 0 rpm
5 seconds 100 rpm
transport of the liquid into cuvettes
50 seconds 720 rpm
measurement at 578 nm.

With the above-described centrifuging program, the wetting agent is first dissolved from fleece 1 for the simplification of the liquid transport. Subsequently, buffer and conjugate fleece are soaked and the components present thereon dissolved. After 300 seconds incubation in the first valve chamber, in which phenytoin binds with the anti-phenytoin-antibody-enzyme conjugate, the equilibrium is adjusted in the next step in the 300 seconds with the spaced and fixed phenytoin present in excess with regard to the sample. The solution is then transported to the substrate fleece, the substrate thereby being dissolved off. The total liquid mixture passes into the cuvette where the extinction decrease is monitored for 50 seconds.

With the help of samples which contain a known amount of phenytoin, a calibration curve is produced according to the above-described process. On the basis of this calibration curve, samples with unknown phenytoin content can be measured in corresponding way.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. Process for detection of a free analyte in a liquid sample comprising incubating said sample with a labeled binding partner for said analyte and one of an immobilized analyte or immobilized analyte analogue, or incubating said sample with one of a labeled analyte or labeled analyte analogue and an immobilized binding partner for said analyte, wherein said binding partner has an affinity for immobilized and labeled analyte or immobilized and labeled analyte analogue greater than affinity for said free analyte, said labeled binding partner, labeled analyte or labeled analyte analogue being present in an amount less than the amount of free analyte in said sample, separating immobilized complex from said liquid and measuring label in either immobilized or liquid phase as a measure of analyte in said sample.

2. Process of claim 1, wherein said immobilized analyte binds to an insoluble carrier by a bridge member, and said binding partner has greater affinity toward said bridge member-bound immobilized analyte than toward said free analyte.

3. Process of claim 1, wherein said analyte analogue is structurally similar to said free analyte.

4. Process of claim 1, wherein said analyte analogue is a portion of said free analyte.

5. Process of claim 1, wherein said labeled binding partner, labeled analyte or labeled analyte analogue and said free analyte are in a ratio of from 1:1 to 1:10000.

6. Process of claim 1, wherein said incubating steps are carried out in sequence.

7. Process of claim 1, wherein said incubating steps are carried out simultaneously.

8. Process of claim 1, wherein said analyte analogue is an anti-idiotype antibody.

9. Process of claim 1, wherein said binding partner is a hapten.

10. Process of claim 1, wherein said binding partner is an antibody.

11. Process of claim 10, wherein said antibody is a monoclonal antibody.

12. Process of claim 10, wherein said antibody is a Fab fragment.

13. Reagent for detecting a free analyte in a liquid sample, comprising one of an immobilized analyte or immobilized analyte analogue and a labeled binding partner for said free analyte or one of a labeled analyte or labeled analyte analogue and an immobilized binding partner, said binding partner having an affinity for labeled or immobilized analyte or analyte analogue greater than for said free analyte.

14. Reagent of claim 13, further comprising a buffer system.

15. Reagent of claim 13, further comprising one or more adjuvants.

16. Reagent of claim 13, further comprising one or more substances for determining said labeled material.

17. Reagent of claim 13, wherein said reagent is in the form of a kit containing separate portions of each component of said reagent.

18. Reagent of claim 17, wherein said components are in solution form.

19. Reagent of claim 17, wherein said components are in the form of carriers.

20. Reagent of claim 17, wherein said components are in powder form.

21. Reagent of claim 17, wherein said components are in tablet form.

22. Reagent of claim 17, wherein said components are lyophilisates.

* * * * *